United States Patent
Hall et al.

(10) Patent No.: US 10,191,016 B2
(45) Date of Patent: Jan. 29, 2019

(54) METHOD AND SYSTEM FOR PASSIVE DETECTION, LOCALIZATION AND CHARACTERIZATION OF MECHANICAL WAVE SOURCES USING ULTRASONIC GUIDED WAVES

(71) Applicant: HIDDEN SOLUTIONS LLC, Kissimmee, FL (US)

(72) Inventors: James Stroman Hall, Orlando, FL (US); Jennifer Emmons Michaels, Tucker, GA (US)

(*) Notice: Subject to any disclaimer, the term of this patent is extended or adjusted under 35 U.S.C. 154(b) by 1019 days.

(21) Appl. No.: 14/396,375

(22) PCT Filed: Mar. 14, 2013

(86) PCT No.: PCT/US2013/031559
§ 371 (c)(1),
(2) Date: Oct. 22, 2014

(87) PCT Pub. No.: WO2013/172962
PCT Pub. Date: Nov. 21, 2013

(65) Prior Publication Data
US 2015/0106037 A1    Apr. 16, 2015

Related U.S. Application Data

(60) Provisional application No. 61/647,763, filed on May 16, 2012.

(51) Int. Cl.
G01M 5/00       (2006.01)
H04W 4/02      (2018.01)
(Continued)

(52) U.S. Cl.
CPC ............. $G01N\ 29/36$ (2013.01); $G01N\ 29/04$ (2013.01); $G01N\ 29/043$ (2013.01);
(Continued)

(58) Field of Classification Search
CPC ........ G01N 29/04; G01N 29/34; G01N 29/36; G01N 2291/0258
See application file for complete search history.

(56) References Cited

U.S. PATENT DOCUMENTS

| | | | | |
|---|---|---|---|---|
| 2003/0009300 A1* | 1/2003 | Giurgiutiu | ............. | G01N 29/11 702/35 |
| 2009/0326834 A1* | 12/2009 | Sundaresan | ......... | G01M 5/0041 702/34 |

(Continued)

OTHER PUBLICATIONS

Sabra, Using cross correlations of turbulent flow-induced ambient vibrations to estimate the structural impulse response. Application to structural health monitoring, The Journal of the Acoustical Society of America 121, 1987 (2007); doi: 10.1121/1.2710463.*

(Continued)

*Primary Examiner* — Michael J Dalbo
(74) *Attorney, Agent, or Firm* — William Lovin & Associates, LLC; William R. Lovin

(57) ABSTRACT

A method and system for passively detecting, localizing, and/or characterizing a mechanical wave source at one or more spatial points of interest on a structure using ultrasonic guided waves are provided. The method includes estimating the spatial channel impulse response at one or more spatial points of interest using a movable transducer. Collected data recorded in response to transient mechanical waves is then combined with the spatial channel impulse response estimates to detect, localize, and/or characterize the source. A direct path from the mechanical wave source to each transducer is not required. Anisotropies and variations between transducer transfer functions may be accounted for and all propagation paths may be used to perform source localization. The method and system may leverage structural complexity rather than ignore it.

18 Claims, 9 Drawing Sheets

(51) Int. Cl.
*G01N 29/04* (2006.01)
*G01N 29/24* (2006.01)
*G01N 29/30* (2006.01)
*G01N 29/34* (2006.01)
*G01N 29/36* (2006.01)
*G01N 29/44* (2006.01)
*H04W 52/02* (2009.01)

(52) U.S. Cl.
CPC ......... *G01N 29/2475* (2013.01); *G01N 29/30* (2013.01); *G01N 29/34* (2013.01); *G01N 29/4427* (2013.01); *G01N 29/4472* (2013.01); *H04W 4/027* (2013.01); *H04W 52/0216* (2013.01); *H04W 52/0251* (2013.01); *G01M 5/0033* (2013.01); *G01M 5/0066* (2013.01); *G01N 2291/0258* (2013.01); *G01N 2291/0425* (2013.01); *G01N 2291/2694* (2013.01); *Y02D 70/00* (2018.01); *Y02D 70/142* (2018.01); *Y02D 70/144* (2018.01); *Y02D 70/146* (2018.01); *Y02D 70/20* (2018.01)

(56) References Cited

U.S. PATENT DOCUMENTS

| | | | |
|---|---|---|---|
| 2010/0217544 A1* | 8/2010 | Yan | G01N 29/07 702/56 |
| 2011/0114412 A1* | 5/2011 | De Lorenzo | G01N 29/07 181/101 |
| 2012/0203474 A1* | 8/2012 | Kawiecki | G01N 29/07 702/39 |
| 2013/0327148 A1* | 12/2013 | Yan | G01N 29/34 73/628 |

OTHER PUBLICATIONS

Moll, Time-varying inverse filtering of narrowband ultrasonic signals, Structural Health Monitoring 10(4) 403-415, 2010.*
Jacob Benesty, Adaptive eigenvalue decomposition algorithm for passive acoustic source localization, The Journal of the Acoustical Society of America 107, 384 (2000); doi: 10.1121/1.428310.*

* cited by examiner

METHOD AND SYSTEM FOR PASSIVE DETECTION, LOCALIZATION AND CHARACTERIZATION OF MECHANICAL WAVE SOURCES USING ULTRASONIC GUIDED WAVES

CROSS-REFERENCE TO RELATED APPLICATIONS

This application claims the priority benefit of U.S. Provisional Application No. 61/647,763, filed May 16, 2012, entitled "Multi-Path Passive Source Localization with Ultrasonic Guided Waves," the entirety of which is hereby incorporated by reference.

BACKGROUND

1. Field of Invention

The invention relates generally to methods and systems for detection, localization, and characterization of defects in a structure, and more particularly, to a method and system for passive detection, localization, and characterization of mechanical wave sources using ultrasonic guided waves.

2. Discussion of Related Art

Acoustic emission (AE) technology has been used for over 50 years to detect and track the initiation or growth of material defects. At the most fundamental level, acoustic emission systems may use permanently attached sensors to provide continuous monitoring of a structure in an attempt to record and analyze transient mechanical waves associated with, for example, the initiation and growth of cracks, dislocation movements, corrosion effects, metal phase transformations, and external impacts. By combining information about the frequency, magnitude, and location of one or more source events with reliable prognosis tools, repairs and replacements can be performed on an as-needed basis, simultaneously reducing maintenance costs and potentially avoiding unforeseen catastrophic failures.

The fundamental challenges associated with such monitoring fall into the general categories of detection, localization and characterization. The detection problem is largely associated with discriminating acoustic or elastic waves emanating from sources of interest from acoustic or elastic waves originating from benign environmental or operational sources. In general, the detection problem may be addressed by, for example, intelligent sensor design, parametric analysis, signal-based analysis, and artificial intelligence methods. In some applications, detection alone may provide sufficient information since the frequency and magnitude of source events has been repeatedly shown to be a strong indicator of impending material failure. In many cases, however, the location of the source event is critical to effective detection since the source location can be used to separate benign events from events of interest.

The source localization challenge may generally be addressed by analyzing the relative amplitude and time-difference-of-arrival (TDOA) of waves simultaneously recorded from multiple sensors. Linear and zonal location techniques may constrain the source location either to a line between two sensors (linear) or a spatial area that is based on sensor placement (zonal). Triangulation methods, for example, may use three or more sensors to triangulate the source using TDOA information. In all cases, it may be the direct-path TDOA information that is combined with assumed or measured propagation velocity profiles and geometric configuration (planar, cylindrical, spherical, etc.) to determine the source location.

While direct path techniques work well for simple structures, such as pressure vessels, this simplified approach to source localization becomes problematic in complex structures, particularly for AE systems that use dispersive guided waves to monitor large, complex, plate-like structures. Structural complexity can result from any number of geometric features, including cut-outs, stiffeners, rivets, thickness variations, and anisotropic materials (e.g. carbon-fiber reinforced plastics). When a structure is complex, guided waves travel in very complex paths via multiple modes and there is often not a direct path between a potential source location and sensors.

Another problem with triangulation TDOA methods is that they require propagation velocity profiles for accurate and reliable source localization. As such, calibration is often performed for structures in which the propagation velocity either varies with location or is unknown due to material or process variability. Calibration data, however, is often obtained through tedious and error-prone manual measurements of received waveforms using, for example, pencil break, glass capillary break, or active transducer sources, which can be very costly and limit localization performance.

Characterization of sources is often problematic, and is usually achieved by ad hoc methods that attempt to correlate measured signal characteristics (e.g., duration, center frequency, etc.) with different damage mechanisms. An alternative approach is based upon a more fundamental understanding of acoustic emission sources, which is related to the actual source mechanism. The source mechanism can be modeled by a source-time function and a directivity pattern, and if these quantities can be estimated, the source can be characterized based upon its physical attributes.

Localization challenges that arise from structural complexities can be mitigated with high sensor density, but this approach is usually not economically viable because of the increased cost and weight. Another alternative to help address complexity is the use of artificial intelligence techniques, such as neural networks. These methods are problematic from several different perspectives. First, since performance is sensitive to training and calibration data, it is difficult to quantify expected performance. Second, there is a discomforting lack of insight into the trained systems since artificial intelligence methods generally do not result in a set of intuitive rules that can be explained, justified, or even documented. Finally, there is a relatively high level of operator training required in order to effectively and reliably train and interpret artificial intelligence systems, which increases the cost and complexity of effective implementation.

SUMMARY

According to an embodiment, a method of estimating a spatial channel impulse response at one or more spatial points of interest on a structure may be provided. The method may include collecting data at one or more spatial points of interest on the structure using a movable transducer. The data collection may include individually exciting at least one transducer on the structure with a known excitation function and recording measurements at the one or more spatial points of interest with the movable transducer. The method may include computing a spatial channel impulse response estimate at the one or more spatial points of interest based on the collected data.

In some embodiments, the computing of a spatial channel impulse response estimate at the one or more spatial points of interest may include decomposing the collected data at the one or more spatial points of interest on the structure into one or more data sets having mode and/or directional specificity.

In some embodiments, the movable transducer may be configured to record measurements including mode and/or directional specificity.

In an embodiment, the computing of a spatial channel impulse response estimate may include deconvolution of the known excitation signal and/or transfer function of the movable transducer.

According to another embodiment, a method of passively detecting, localizing, and/or characterizing one or more mechanical wave sources located at one or more spatial points of interest on a structure may be provided. The method may include obtaining a spatial channel impulse response estimate at the one or more spatial points of interest, collecting data from at least one transducer on the structure in response to one or more mechanical wave source events; and combining the collected data with one or more spatial channel impulse response estimates to detect, localize, and/or characterize one or more mechanical wave sources at the one or more spatial points of interest on the structure. In some embodiments, the combining the collected data with spatial channel impulse response estimates may include utilizing deconvolution, cross-correlation, weighted cross-correlation, regularized deconvolution, Weiner deconvolution, or other mathematically equivalent operations.

According to another embodiment, a system for detecting, localizing, and/or characterizing a source of mechanical waves at one or more spatial points of interest on a structure may be provided. The system may include at least one transducer on the structure, wherein the at least one transducer is configured to record a signal received from one or more mechanical wave source events on the structure. The system may include a storage device containing a spatial channel impulse response estimate for each of the one or more spatial points of interest on the structure. A processor coupled to the at least one transducer may be configured to collect data from the at least one transducer and combine the collected data with the stored one or more spatial channel impulse response estimates to detect, localize, and/or characterize the unknown mechanical wave source at the one or more spatial points of interest on the structure. The collected data may include the recorded signal received from the one or more mechanical wave source events on the structure.

In some embodiments, the at least one transducer may include a plurality of transducers spaced from one another on the structure. One or more of the plurality of transducers may be configured to record signals received from the one or more mechanical wave source events.

In some embodiments, the system may include a movable transducer configured to record measurements taken at the one or more spatial points of interest during individual excitation of the at least one transducer according to a known excitation function. The processor may be configured to collect other data at the one or more spatial points of interest on the structure by receiving and processing measurements taken using the movable transducer at the one or more spatial points of interest during individual excitement of the at least one transducer. The processor may be configured to compute a spatial channel impulse response estimate at each of the one or more spatial points of interest based on the collected other data at the one or more spatial points of interest on the structure.

Further features and advantages, as well as the structure and operation of various embodiments of the invention, are described in detail below with reference to the accompanying drawings.

BRIEF DESCRIPTION OF THE DRAWINGS

The foregoing and other features and advantages of the invention will be apparent from the following, more particular description of some example embodiments of the invention, as illustrated in the accompanying drawings. Unless otherwise indicated, the accompanying drawing figures are not to scale. Several embodiments of the invention will be described with respect to the following drawings, in which like reference numerals represent like features throughout the figures, and in which.

DETAILED DESCRIPTION

Some embodiments of the invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the invention. All references cited herein are incorporated by reference as if each had been individually incorporated.

Figure 1:
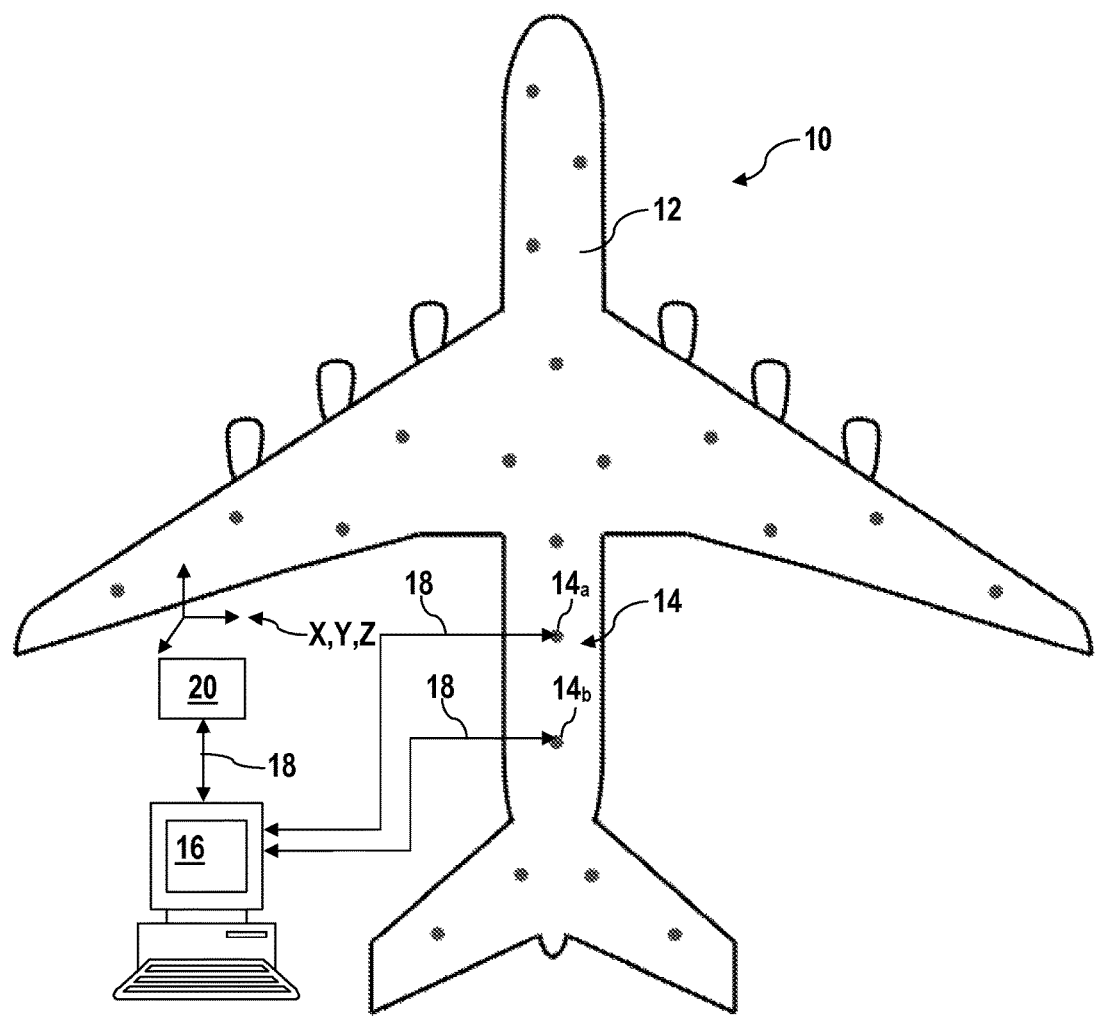
FIG. 1 is a schematic representation of a spatially distributed array of transducers mounted on an aircraft structure illustrating a potential practical application of the system and method for passive detection, localization, and characterization of mechanical wave sources with ultrasonic guided waves according to an embodiment of the invention.

FIG. 1 is a schematic representation of a system 10 for multi-path passive detection, localization and/or characterization of mechanical wave sources using ultrasonic guided waves according to an embodiment of the invention. As shown in FIG. 1, the system 10 may include a spatially distributed array 14 of transducers 14a, 14b, etc., mounted on a structure 12 such as, for example but not limited to, an aircraft structure. Other structures may include, for example but not limited to, metallic and composite aerospace components, marine vessel hulls, as well as civil, nuclear, and petrochemical infrastructure to name but a few. Each transducer 14a, 14b, etc. may be coupled via a communication link 18 to a computer 16 having a processor. A movable transducer 20 may also be provided for taking and recording measurements at one or more spatial points of interest on the structure 12. The movable transducer 20 may be a non-contact vibration measurement device or sensor arranged to be moved in one or more dimensions along axes X, Y, Z as shown schematically in FIG. 1. The movable transducer 20 may be coupled via a communication link 18 to the computer 16. Computer 16 may transmit instructions (signals) to and receive data from the array 14 and the movable transducer 20 via communication links 18. Communication links 18 may be wired or wireless.

In the embodiment depicted in FIG. 1, the spatially distributed array 14 may be permanently attached on the aircraft structure 12. The location of each transducer 14a, 14b, etc. may be prescribed or arbitrary; there are no restrictions regarding an array pattern or proximity to structural features or other transducers. A sufficient number of transducers 14, for example one or more transducers, may be distributed throughout the structure 12 so that mechanical waves originating from any location or spatial point of interest (e.g., potential source location) can be sensed by one or more of the transducers 14a, 14b, etc. In the embodiment of FIG. 1, each transducer 14a, 14b, etc. in the spatially distributed array 14 may be, for example but not limited to, an inexpensive piezoelectric transducer which may be permanently attached to the structure 12, either through adhesive bonding or embedding the sensors within the structure 12 itself. The distributed array 14 need not be permanently attached to the structure 12. The transduction mechanism of transducer 14a, 14b, etc., may or may not be piezoelectric in nature.

Mechanical waves may originate from the structure through a wide range of phenomena or events. Mechanical waves may originate, for example, from the acoustic emissions associated with the release of localized stress energy in the structure or external impacts. Exemplary mechanical wave source events originating in the structure may include, for example but not limited to, the initiation and growth of cracks, dislocation movements, corrosion effects, metal phase transformations, and external impacts.

Figure 2:
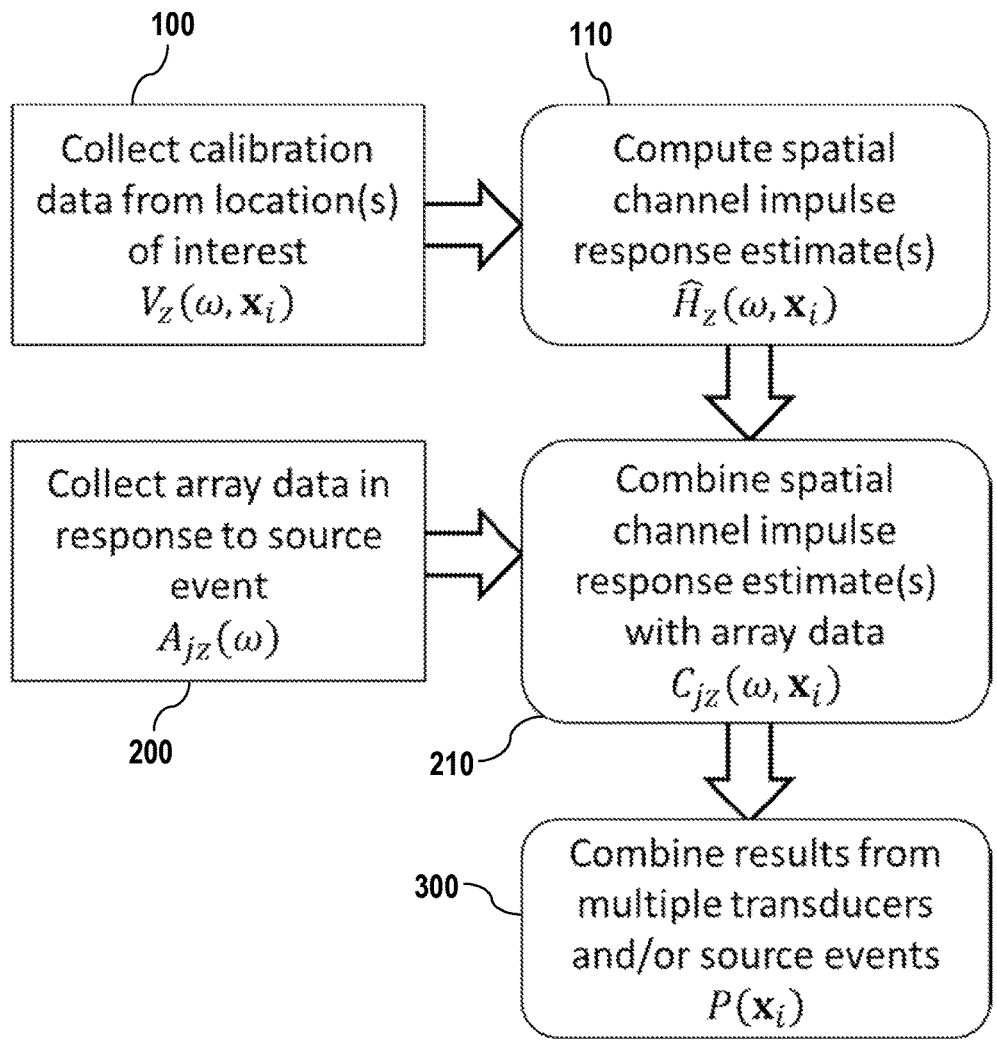
FIG. 2 illustrates a flow chart depicting a method of detecting and localizing a source of mechanical waves at one or more spatial points of interest on a structure according to an embodiment of the invention.

FIG. 2 illustrates a flow chart depicting a method of detecting and localizing a source of mechanical waves at one or more spatial points of interest on a structure 12 according to an embodiment of the invention. The method depicted in FIG. 2 may, for example, be carried out utilizing the system 10 described above and shown in FIG. 1. The flow chart in FIG. 2 includes steps of the method for the case of a single propagating mode and a uniform source according to an embodiment of the invention. In FIG. 2, steps 100 and 200 (shown in blocks with square corners) indicate data collection/acquisition steps, while steps 110, 210, 300 (shown in blocks with rounded corners) correspond to calculation/computation steps. The data acquisition steps (100, 200) and computation steps (110, 210, 310) are described in detail below using a frequency-domain model. The use of a frequency-domain model was chosen for readibility and the concepts described herein are equally applicable to implementations using equivalent or alternative domains, such as time, spatial, or wavenumber domains.

As shown in the example method depicted in FIG. 2, two sets of data may be collected to perform source localization. In step 100, calibration data, $V_z(\omega, x_i)$, may be collected from spatial locations of interest, $x_i$, on the structure 12 using a movable transducer 20 (see FIG. 1) prior to placing structure 12 into service (operation). In step 200, array data, $A_{jz}(\omega)$, may be collected from the transducer array 14, while the structure 12 is in service (operation).

Figure 3:
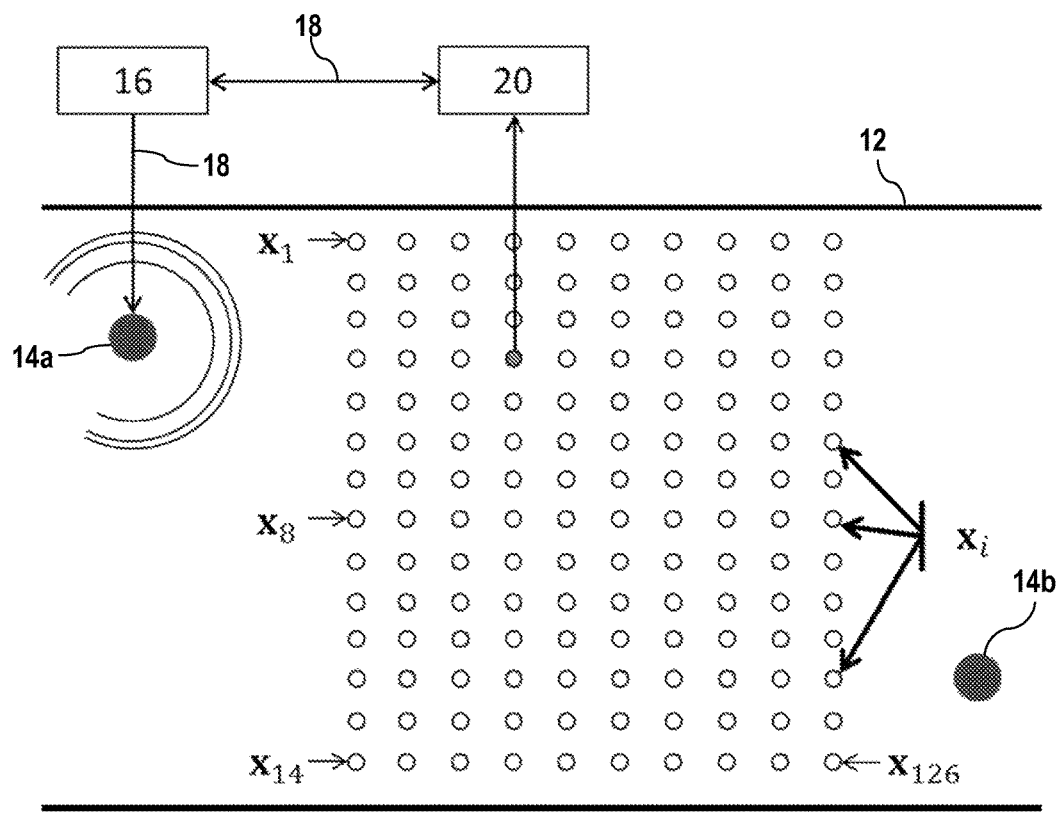
FIG. 3 is an illustrative and schematic depiction of excitation of a transducer of the array of transducers and collecting data at the one or more spatial points of interest on the structure using a movable transducer according to an embodiment.

In step 100 in FIG. 2, data may be collected from spatial locations of interest $x_i$ on the structure 12 by the movable transducer 20. FIG. 3, for example, graphically depicts collection of the $V_z(\omega, x_i)$ measurements by the movable transducer 20 (step 100). Each measurement may be obtained from a location of interest, $x_i$, while the zth transducer z (e.g., transducer 14a) acts as a transmitter. That is, computer 16 may output a known excitation signal via communication link 18 to transducer 14a, which in turn generates mechanical waves (e.g., ultrasonic guided waves) in the structure 12. The movable transducer 20 may be controlled by the computer 16 to move relative to the structure 12 to record measurements from any number of spatial points of interest $x_i$. Measurements can be taken by the movable transducer 20 in whatever density or pattern is desired; they need not be taken on a grid or at any specific spatial interval. The movable transducer 20 may be any suitable sensor known in the art such as, for example but not limited to, a scanning laser vibrometer (SLV) and/or a scanning air-coupled ultrasonic transducer (SAUT), and may be used to efficiently obtain $V_z(\omega, x_i)$ measurements from one or more locations of interest $x_i$ on the structure 12.

Figure 4:
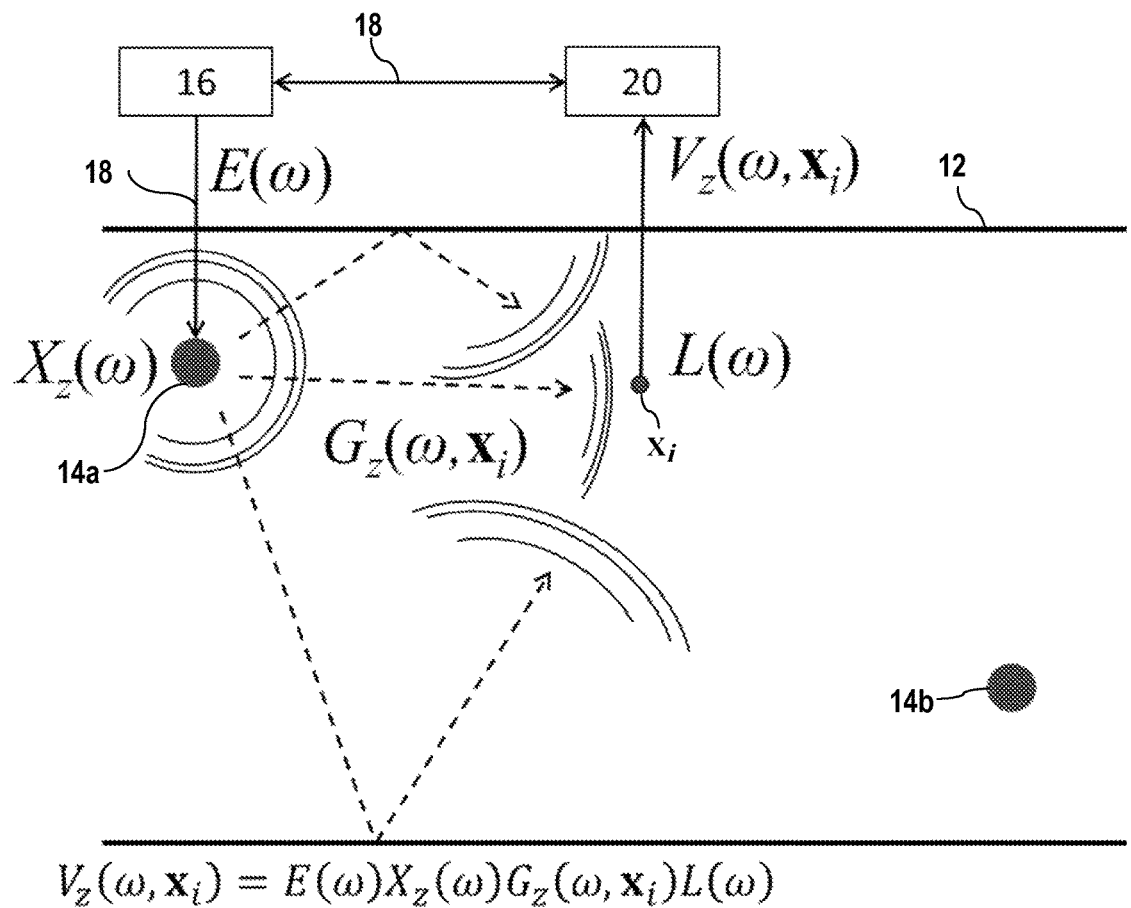
FIG. 4 is an illustrative depiction of a mathematical model used to describe the transducer excitation, multi-path propagation, and measurement of mechanical waves at the one or more spatial points of interest using the movable transducer according to an embodiment.

A mathematical model used to describe these $V_z(\omega, x_i)$ measurements is:

$$V_z(\omega, x_i) = E(\omega) X_z(\omega) G_z(\omega, x_i) L(\omega), \quad (1)$$

where $\omega$ is the radian frequency; $E(\omega)$ is the source function or known excitation function, corresponding to the electrical signal sent to transducer z from computer 16, and is considered known in the methods and systems described herein; $X_z(\omega)$ is the transducer transfer function for transducer z, which describes the transduction from electrical to mechanical waves; $G_z(\omega, x_i)$ is the Green's function that encompass all paths from transducer z to location of interest $x_i$, including dispersion, propagation loss, and geometric scattering effects; and finally, $L(\omega)$ describes the transfer function from mechanical waves to electrical energy for the movable sensor. FIG. 4 illustrates the individual excitation of transducer 14a of the transducer array 14 on the structure 12 and measurement of the mechanical waves at one of the spatial points of interest $x_i$ using the movable transducer 20 according to an embodiment.

Since the excitation function, $E(\omega)$, is known and the movable sensor transfer function, $L(\omega)$, can be estimated experimentally, these values can be, for example, deconvolved from the $V_z(\omega, x_i)$ measurements to obtain a combined estimate of the transducer transfer function and Green's function (step 110):

$$\hat{H}_z(\omega, x_i) = \frac{V_z(\omega, x_i)}{E(\omega)L(\omega)} \approx X_z(\omega)G_z(\omega, x_i). \tag{2}$$

In many scenarios, $L(\omega) \approx 1$, allowing the $L(\omega)$ term to be ignored.

The combined estimate of the Green's function and transducer transfer function product contained in $\hat{H}_z(\omega, x_i)$, may be referred to as a spatial channel impulse response estimate, and may represent the entire propagation environment from the excitation source (e.g., transducer 14a) to location $x_i$, including electromechanical conversion by the zth transducer, guided wave formation, anisotropic characteristics of the sensor, reflections, dispersion, and attenuation. If reciprocity is assumed, then the $\hat{H}_z(\omega, x_i)$ term may also describe the entire propagation environment from an isotropic out-of-plane source at location $x_i$, to the zth sensor, to a receiver. The spatial channel impulse response estimate may therefore provide a tremendous amount of information about the propagation environment and may serve as an enabling technology for multi-path source localization. In addition, the spatial channel impulse response estimate can be used, for example, with conventional AE technology as a velocity profile, thereby avoiding manual calibration methods that are both costly and error-prone.

Figure 5:
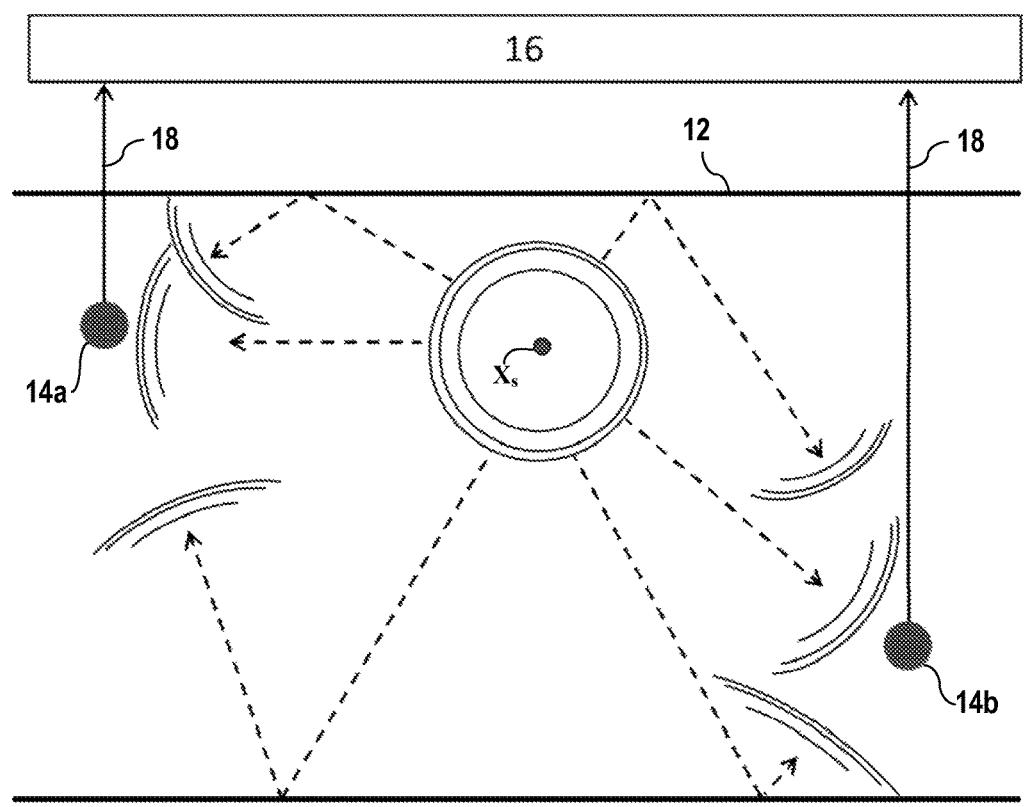
FIG. 5 is an illustrative depiction of a mechanical wave originating from a source location, propagating throughout the structure, and arriving at two transducers on the structure according to an embodiment.

FIG. 5 illustrates mechanical waves originating from an unknown source location, $x_s$, while the structure 12 is in service. These waves will propagate throughout the structure 12, possibly interacting with one or more geometric features of the structure 12 and may be measured by one or more of the transducers 14 for processing, as indicated in step 200 in FIG. 2.

Measurements from the transducer array 14 may be continuously monitored to identify the presence of mechanical waves associated with a source event. Data may be recorded from the one or more transducers 14 over a finite amount of time, both preceding and following a specific time reference. Establishment of a specific time reference may performed, for example, by a threshold crossing at the zth transducer (e.g., upon measuring mechanical waves which satisfy and/or exceed some predetermined condition or threshold level). Alternative methods for data acquisition will be familiar to one skilled in the art.

A frequency-domain model that describes the data recorded from the zth transducer in response to a jth source event is as follows:

$$A_{jz}(\omega) = S_j(\omega)H_z(\omega), \tag{3}$$

where the source-time function, $S_j(\omega)$, corresponds to a point-like isotropic source located at $x_s$, and $H_z(\omega)$ is a spatial channel impulse response that accounts for multi-path propagation, dispersion, attenuation, and sensor directivity. Data recorded from the zth transducer may also be dependent on the directivity of the source, which will vary with source type. For readability, this embodiment only accounts for anisotropies of the transducer through the $H_z(\omega)$ transfer function; the source is assumed to be a point-like, or uniform, source. An additional embodiment that accounts for anisotropic sources is described in further detail below.

The number of $A_{jz}(\omega)$ signals recorded for each source event may not correspond to the total number of transducers in the structure, since it is possible but unlikely that all sensors will be sensitive to all areas of interest in a large structure. At a minimum, a single $A_{jz}(\omega)$ signal is required.

Mathematically, the spatial channel impulse response $H_z(\omega)$ may be expressed as follows for a point-like source:

$$H_z(\omega) = X_z(\omega)G_z(\omega, x_s), \tag{4}$$

where $G_z(\omega, x_s)$ is a Green's function that describes the multi-path guided wave propagation, dispersion, and attenuation from the unknown source location, $x_s$, to the zth transducer.

To facilitate source localization, the spatial channel impulse response estimates, $\hat{H}_z(\omega, x_i)$ may be combined with the array data, $A_{jz}(\omega)$ (step 210). This operation may be implemented via any number of different mechanisms including, for example but not limited to, cross-correlation, deconvolution, weighted cross-correlation, or regularized deconvolution.

In an example embodiment of step 210, cross-correlation can be used to combine datasets. Cross-correlation between the array data $A_{jz}(\omega)$ and a spatial channel impulse response estimate $\hat{H}_z(\omega, x_i)$ at location $x_i$ using transducer z may be computed as:

$$C_{jz}(\omega, x_i) = A_{jz}(\omega)\hat{H}_z^*(\omega, x_i), \tag{5}$$

where $C_{jz}(\omega, x_i)$ is the combined signal for the jth source event and the superscript "*" indicates a complex conjugate operation. The above equation can rewritten as:

$$C_{jz}(\omega, x_i) = S_j(\omega)Y_z(\omega, x_i), \tag{6}$$

where $$Y_z(\omega, x_i) = H_z(\omega)\hat{H}_z^*(\omega, x_i). \tag{7}$$

In the above Eq. (7), if $\hat{H}_z(\omega, x_i)$ exactly matches $H_z(\omega)$, which is only expected if $x_i = x_s$, then $Y_z(\omega, x_i)$ will be real valued. If $\hat{H}_z(\omega, x_i)$ does not match $H_z(\omega)$, however, then $Y_z(\omega, x_i)$ will comprise complex values with random phase and magnitude.

The combined signals from each transducer can then be consolidated to produce a single pixel value for the jth source event, $P_j(x_i)$ (step 300):

$$P_j(x_i) = \int \left| \sum_z \alpha_z C_{jz}(\omega, x_i) \right|^2 d\omega, \tag{8}$$

where $\alpha_z$ is a weighting coefficient and $\Sigma_z$ indicates a summation over all transducer pairs. Substituting Eq. (6) into Eq. (8) and collecting $S_j(\omega)$ terms yields:

$$P_j(x_i) = \int \left| S_j(\omega) \sum_z \alpha_z Y_z(\omega, x_i) \right|^2 d\omega. \tag{9}$$

In the above equation, if $x_i = x_s$, then the $Y_z(\omega, x_i)$ will sum coherently to produce a large, real-valued term. In contrast, if $x_i \neq x_s$ then the $Y_z(\omega, x_i)$ will not be in-phase with one another and will destructively interfere during summation, resulting in a small, random-phase term. Consequently, the $P_j(x_i)$ term is expected to be large when $x_i = x_s$ and small otherwise.

The weighting coefficient may be uniform over all transducer pairs or may be computed adaptively to improve source localization results. For example, the weighting coefficients can be used to normalize the combined signals to have consistent power levels and/or to incorporate adaptive techniques such as MUSIC, maximum likelihood, or minimum variance techniques as disclosed in, for example, J. S. Hall and J. E. Michaels, "Minimum variance ultrasonic imaging applied to an in situ sparse guided wave array," *IEEE Trans. Ultrason., Ferroelectr., Freq. Control*, 57 (10), pp. 2311-2323 (2010) and J. S. Hall and J. E. Michaels, "Computational efficiency of ultrasonic guided wave imaging algorithms," *IEEE Trans. Ultrason., Ferroelectr., Freq. Control*, 58 (1), pp. 244-248 (2011), both of which are hereby incorporated by reference.

While the values obtained in Eq. (8) can be used directly, it is customary to combine localization results from multiple source events. The use of multiple source events provides a higher degree of certainty for source localization and can help to discriminate between multiple source locations. Multiple source events can be combined by simply summing the $P_j(x_i)$ values (step 300 in FIG. 2):

$$P(x_i) = \sum_j P_j(x_i). \tag{10}$$

The values computed in Eq. (10) represent the relative likelihood of a source located at each spatial point of interest $x_i$. These values can either be presented as an image to facilitate interpretation and localization, or interpreted directly for automated source detection and localization.

In another embodiment of step 210, Wiener deconvolution can be used to combine the array data $A_{jz}(\omega)$ with spatial channel impulse response estimates $\hat{H}_z(\omega,x_i)$. In this case, the $C_{jz}(\omega,x_i)$ function may be computed using Weiner deconvolution as:

$$C_{jz}(\omega, x_i) = \frac{A_{jz}(\omega)\hat{H}_z^*(\omega, x_i)}{\hat{H}_z(\omega, x_i)\hat{H}_z^*(\omega, x_i) + \sigma}, \tag{11}$$

where $\sigma$ is a regularization parameter. Similar to the cross-correlation embodiment, Eq. (11) can rewritten as in Eq. (6). With this Weiner deconvolution embodiment, however, the $Y_z(\omega,x_i)$ term in Eq. (6) is defined as:

$$Y_z(\omega, x_i) = \frac{H_z(\omega)\hat{H}_z^*(\omega, x_i)}{\hat{H}_z(\omega, x_i)\hat{H}_z^*(\omega, x_i) + \sigma}. \tag{12}$$

As with cross-correlation, the $Y_z(\omega,x_i)$ values are only expected to be a real-valued if $x_i=x_s$, and consequently, $\hat{H}_z(\omega,x_i)=H_z(\omega)$. The pixel value computation in step 300 can then be performed as described in Eqs. (8) and (10).

In addition to producing real-valued $Y_z(\omega,x_i)$ values, if $C_{jz}(\omega,x_i)$ is computed as in Eq. (11) and $\hat{H}_z(\omega,x_i)=H_z(\omega)$, then the $Y_z(\omega,x_i)$ will also be approximately uniform, resulting in a relatively time-compact version of $C_{jz}(\omega,x_i)$. An alternative embodiment of step 300 can therefore be constructed to take advantage of this effect. To illustrate, the computation of $P_j(x_i)$ can be performed as follows:

$$P_j(x_i) = \max\left|\sum_z \alpha_z \mathfrak{F}^{-1}(C_{jz}(\omega, x_i))\right|^2, \tag{13}$$

where $\mathfrak{F}^{-1}$ indicates an inverse Fourier transform. Eq. (13) converts each combined signal into the time domain, performs a weighted summation to produce a single time-domain signal, and then uses the maximum squared magnitude value of the weighted summation result as $P_j(x_i)$.

In another embodiment, windowing can be performed in the time domain during step 300. In this embodiment, the computation of $P_j(x_i)$ is performed as follows:

$$P_j(x_i) = \int_{\tau_1}^{\tau_2} \left|\sum_z \alpha_z \mathfrak{F}^{-1}(C_{jz}(\omega, x_i))\right|^2 d\tau. \tag{14}$$

An advantage of using a max function, as in Eq. (13), or time-domain windowing, as in Eq. (14), is that computation of the $P_j(x_i)$ value is less dependent on coherent addition of multiple combined signals. Consequently, the embodiments for step 300 shown in the previous two equations may allow for source detection, localization, and characterization using fewer transducers. Additional embodiments that perform essentially the same function will also be apparent to those skilled in the art.

In another embodiment, the deconvolution performed in Eq. (2) can be foregone to minimize computational demands. In this embodiment, the spatial channel impulse response estimate, $\hat{H}_z(\omega,x_i)$, computed in (step 110) is defined as:

$$\hat{H}_z(\omega,x_i)=V_z(\omega,x_i), \tag{15}$$

where $V_z(\omega,x_i)$ is substantially unprocessed. All other operations can be performed as described in the previous embodiments. This specific optimization is possible because the combined signals can be decomposed into the following form:

$$C_{jz}(\omega,x_i)=S_j(\omega)E(\omega)L(\omega)Y_z(\omega,x_i), \tag{16}$$

When computed as in Eq. (8), the above formulation of $C_{jz}(\omega,x_i)$ translates to $P_j(x_i)$ values with the following form (step 300):

$$P_j(x_i) = \int \left|S_j(\omega)E(\omega)L(\omega)\sum_z \alpha_z Y_z(\omega, x_i)\right|^2 d\omega. \tag{17}$$

As with previously described embodiments, if $x_i=x_s$, then the $Y_z(\omega,x_i)$ will sum coherently to produce a large, real-valued term and will destructively interfere otherwise. Other optimizations and simplifications will also be apparent to those skilled in the art and, accordingly, will not be explained further herein.

Figure 6:
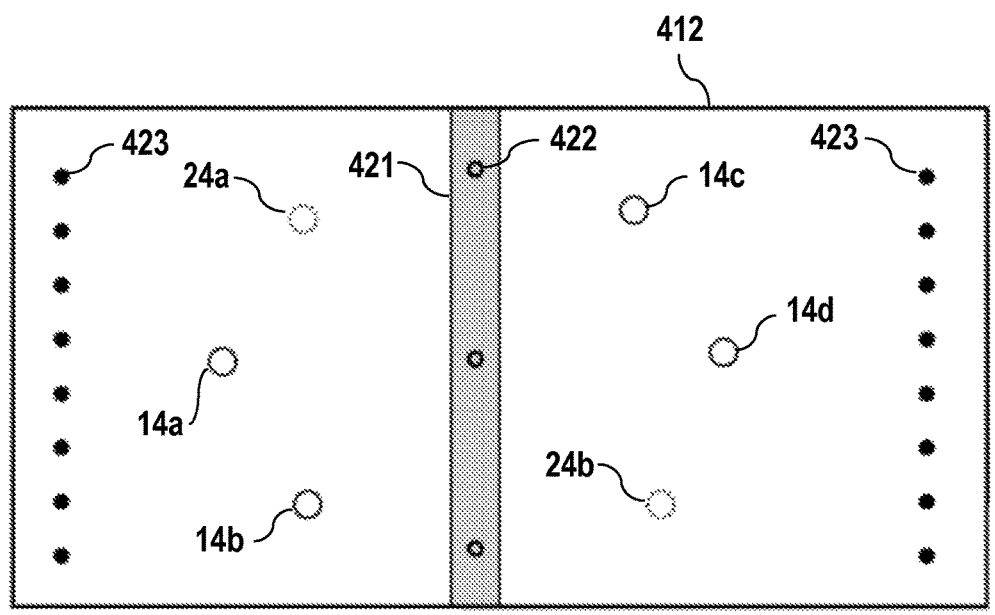
FIG. 6 schematically depicts an experimental plate structure including a spatially distributed array of transducers and various structural features according to an exemplary embodiment.

FIG. 6 schematically depicts a plate structure 412 including a spatially distributed array of transducers 14*a-d* and 24*a, b* and various structural features according to an exemplary embodiment. The plate structure 412 represents a 292×597×3.175 mm aluminum 6061 plate that includes a bonded doubler 421, three fasteners 422, and sixteen through-holes 423. The relatively small size of the plate 412 serves to create a large number of edge reflections. Six piezoelectric transducers 14*a-d* and 24*a, b*, each with a resonant frequency of 300 kHz, are shown permanently attached to the plate 412 in an approximately circular pattern, with three on each side of the doubler 421. Four transducers (14*a-d*) are used as part of a transducer array 14 for source localization, while the two remaining transducers 24*a,* 24*b* act as sources 24 to be localized. The $V_z(\omega,x_i)$ measurements may be collected on a 14×10 mm grid using a SLV, producing 626 separate signals for each of the four array transducers 14*a-d*. A 250 kHz 7-cycle Hann-windowed toneburst may be used as the source excitation for all data acquisition, including mechanical wave source events originating from the two remaining transducers 24a, b.

Figure 7:
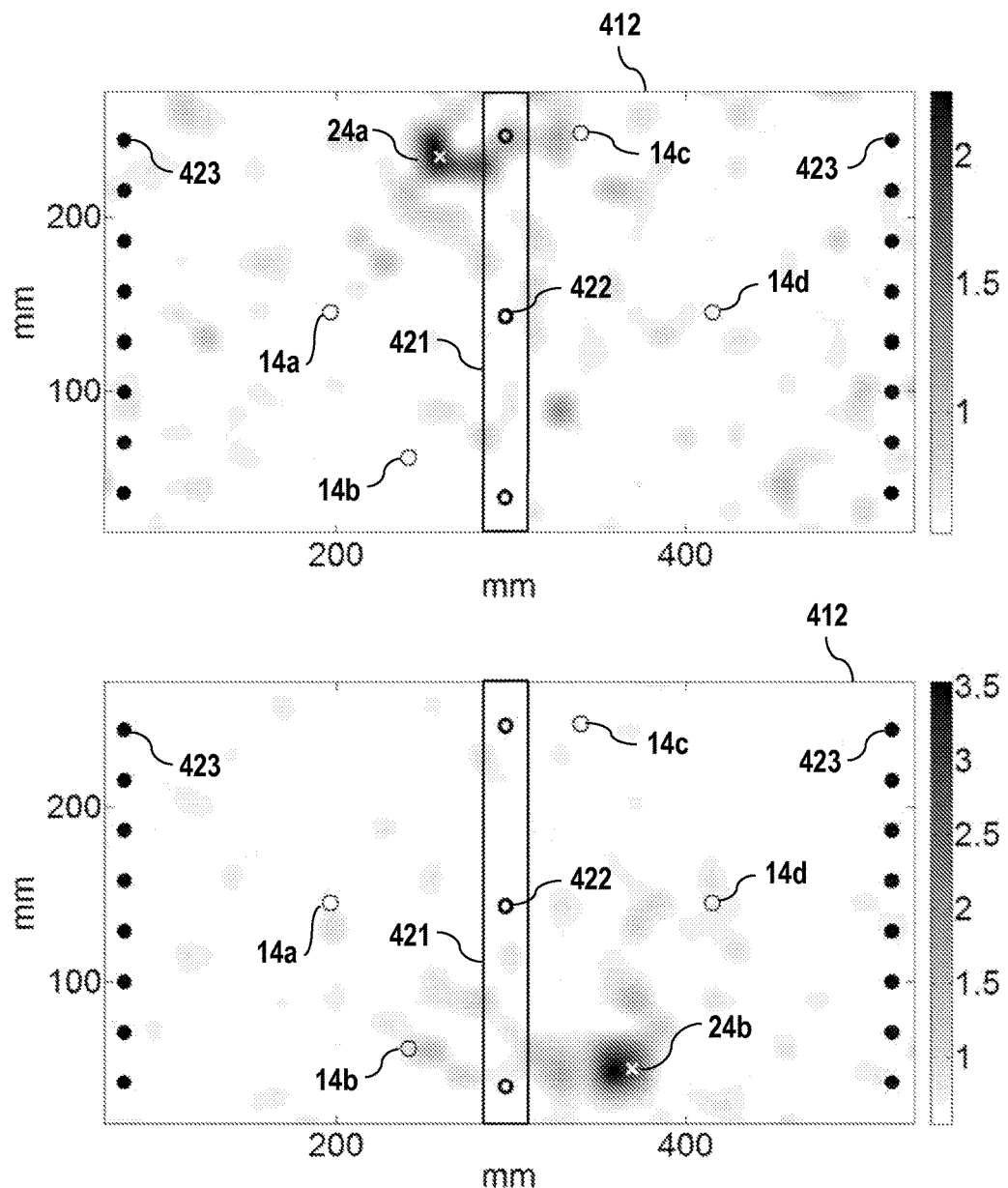
FIG. 7 shows two images generated from measurements recorded at four transducers on the experimental plate structure of FIG. 6 in response to mechanical wave sources positioned at two separate locations on the experimental plate structure.

FIG. 7 shows two images generated from measurements recorded at four transducers 14a-d on the plate structure 412 of FIG. 6 in response to mechanical wave sources 24a,b positioned at two separate locations on the plate structure 412. The images were generated using Eq. (2) for step 110, Eq. (11) for 210, and Eq. (13) for 300. Weighting coefficients were assigned as the inverse of the combined signal power, effectively normalizing each combined signal prior to summation. The source locations 24 are clearly identified in FIG. 7, demonstrating that source localization can be performed on a complex plate with as few as four transducers.

The previous embodiment descriptions have inherently assumed that the source will emit mechanical waves uniformly from the unknown source location $x_s$. This has been found to be a reasonable assumption for point-like sources, however, some sources can be highly directional. In another embodiment, the method and system can be expanded to accommodate both multi-mode propagation and directional sources. Two primary benefits to incorporating this information into the method and system may include: (1) the additional information may improve the ability of the invention to localize sources and (2) it may enable the method and system to characterize sources.

Figure 8:
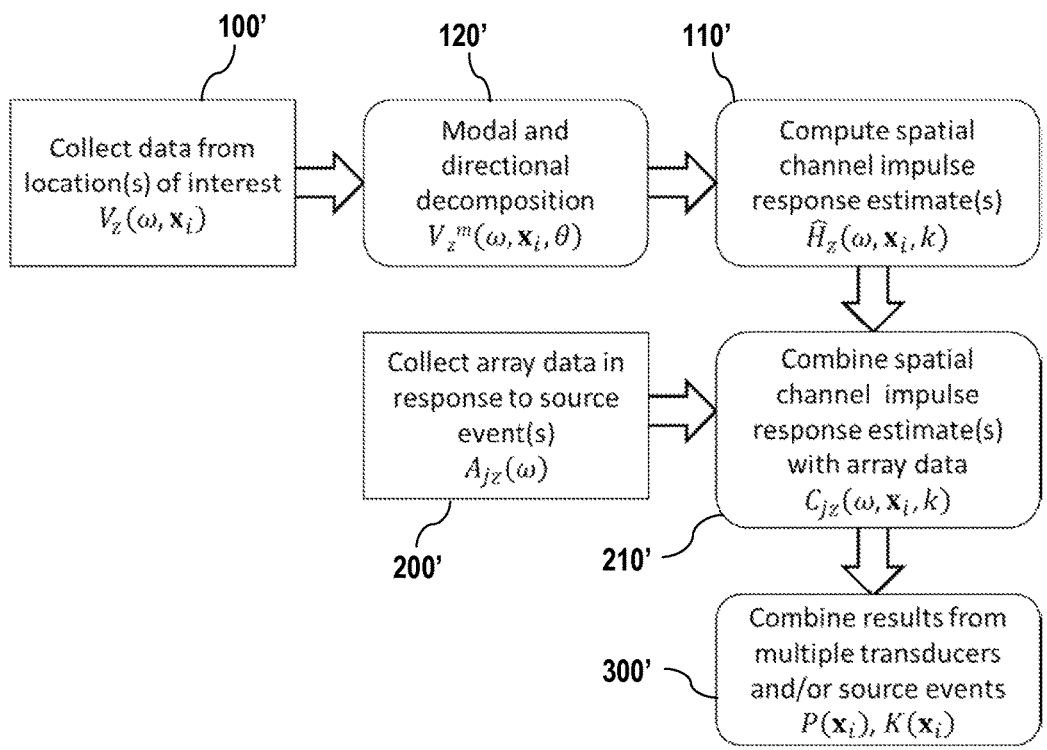
FIG. 8 illustrates a flow chart depicting a method of detecting, localizing, and characterizing a source of mechanical waves at one or more spatial points of interest on a structure for the case of a directional source with multi-mode propagation according to an embodiment.

FIG. 8 illustrates a flow chart depicting a method of detecting, localizing, and characterizing a source of mechanical waves at one or more spatial points of interest on a structure 12 for the case of multi-mode propagation and directional sources according to an embodiment. FIG. 8 is analogous to FIG. 2 except that it includes a step 120' related to modal and directional decomposition. The embodiment shown in FIG. 2 is a simplified case of the embodiment shown in FIG. 8.

In order to accommodate multi-mode propagation and directional scattering, the $V_z(\omega, x_i)$ data may be decomposed into both directional and modal components (step 120') as shown in FIG. 8. The decomposition method can be performed, for example, through physical selectivity during data acquisition, e.g. mode or directional specific sensors, or through advanced signal processing methods, e.g. spatial-domain filtering techniques as disclosed, for example, in T. E. Michaels, J. E. Michaels, and M. Ruzzene, "Frequency-wavenumber domain analysis of guided wavefields," *Ultrasonics*, 51 (4), pp. 452-466 (2011), hereby incorporated by reference. Regardless of the decomposition method, the $V_z(\omega, x_i)$ data is assumed to be decomposed into $V_z^m(\omega, x_i, \theta)$ components, where $\theta$ corresponds to the propagation direction and m indicates the propagation mode.

The following equation expands the propagation model provided in Eq. (3) to accommodate directional sources and multi-mode propagation:

$$A_{jz}(\omega) = \sum_m \int_{-\pi}^{\pi} S_j^m(\omega, \theta) X_z^m(\omega) G_z^m(\omega, x_s, \theta) d\theta, \qquad (18)$$

where the m superscript identifies a propagating mode, e.g. $S_0$ or $A_0$, and $S_j^m(\omega, \theta)$ is the source-time function corresponding to the mth propagating mode emanating from source location $x_s$ in the $\theta$ direction for the jth source event. Let $S_j^m(\omega, \theta)$ be defined as the product of two functions:

$$S_j^m(\omega, \theta) = S_j(\omega)\beta^m(\omega, \theta), \qquad (19)$$

where $\beta^m(\omega, \theta)$ is a transfer function that describes the relationship between an underlying source-time function and the source-time function that emanates in the $\theta$ direction. Estimates of the frequency- and mode-dependent directivity pattern, $\beta^m(\omega, \theta)$, can be obtained via closed form solutions, finite element modeling, or experimental methods that would be understood by one of skill in the art and, accordingly, are not explained further herein.

Equation (18) can be re-written using Eq. (19) as:

$$A_{jz}(\omega) = S_j(\omega) \sum_m \int_{-\pi}^{\pi} \beta^m(\omega, \theta) X_z^m(\omega) G_z^m(\omega, x_s, \theta) d\theta. \qquad (20)$$

The above formulation now agrees with the $A_{jz}(\omega)$ defined as in Eq. (3) where $H_z(\omega)$ is defined as:

$$H_z(\omega) = \sum_m \int_{-\pi}^{\pi} \beta^m(\omega, \theta) X_z^m(\omega) G_z^m(\omega, x_s, \theta) d\theta. \qquad (21)$$

Source localization for a directional source is performed by computing the spatial channel impulse response estimate (step 110') as:

$$\hat{H}_z(\omega, x_i, k) = \frac{\sum_m \int_{-\pi}^{\pi} V_z^m(\omega, x_i, \theta)\beta_k^m(\omega, \theta) d\theta}{E(\omega)L(\omega)}, \qquad (22)$$

where $\hat{H}_z(\omega, x_i, k)$ is the spatial channel impulse response estimate for the kth potential source type located at $x_i$ and $\beta_k^m(\omega, \theta)$ provides mode- and frequency-dependent directivity information about the kth potential source type It is important to note that Eqs. (4) and (2) are simply degenerate cases of Eq. (21) and (22), respectively, wherein the source radiates mechanical waves in a uniform pattern and only a single propagating mode is present. Mathematically, this scenario can be described as:

$$\beta_k^m(\omega, \theta) = \begin{cases} 1 & \text{when } m = 0 \\ 0 & \text{otherwise} \end{cases}, \qquad (23)$$

$$G_z^m(\omega, x_s, \theta) = \frac{1}{2\pi} G_z(\omega, x_s), \text{ and} \qquad (24)$$

$$V_z^m(\omega, x_s, \theta) = \frac{1}{2\pi} V_z(\omega, x_s). \qquad (25)$$

Source-specific spatial channel impulse response estimates, $\hat{H}_z(\omega, x_i, k)$, can be combined with array data, $A_{jz}(\omega)$ in the same manner as illustrated, for example, in Eq. (5) or (11) (step 210'). The difference between step 210' and step 210 is that each of the combined signals will be source-specific, e.g. $C_{jz}(\omega, x_i, k)$.

Source localization with mode- and frequency-dependent directivity patterns can be performed in a variety of methods (step 300'). In one embodiment, the computation of the relative likelihood of a source $x_i$ can be performed by first computing the relative likelihood of a specific source type at $x_i$, similar to Eq. (8):

$$P_j(x_i, k) = \int \left| \sum_z \alpha_z C_{jz}(\omega, x_i, k) \right|^2 d\omega. \quad (26)$$

The $P_j(x_i)$ value is then determined by finding the maximum $P_j(x_i,k)$ value:

$$P_j(x_i) = \max_k P_j(x_i, k). \quad (27)$$

The above formulation may produce a large magnitude $P_j(x_i)$ when one of the potential sources is located at $x_i$. As before, the values computed in Eq. (27) can be combined with data from other source events, as in Eq. (10). The final result can either be presented as an image to facilitate interpretation and localization, or interpreted directly for automated localization. Source characterization is performed by identifying the most likely source type at any given location, $K_j(x_i)$, which can be identified, for example, by:

$$K_j(x_i) = k \text{ such that } P_j(x_i, k) = \max_n P_j(x_i, n). \quad (28)$$

These and other methods for performing source characterization will be understood by one having ordinary skill in the art.

Figure 9:
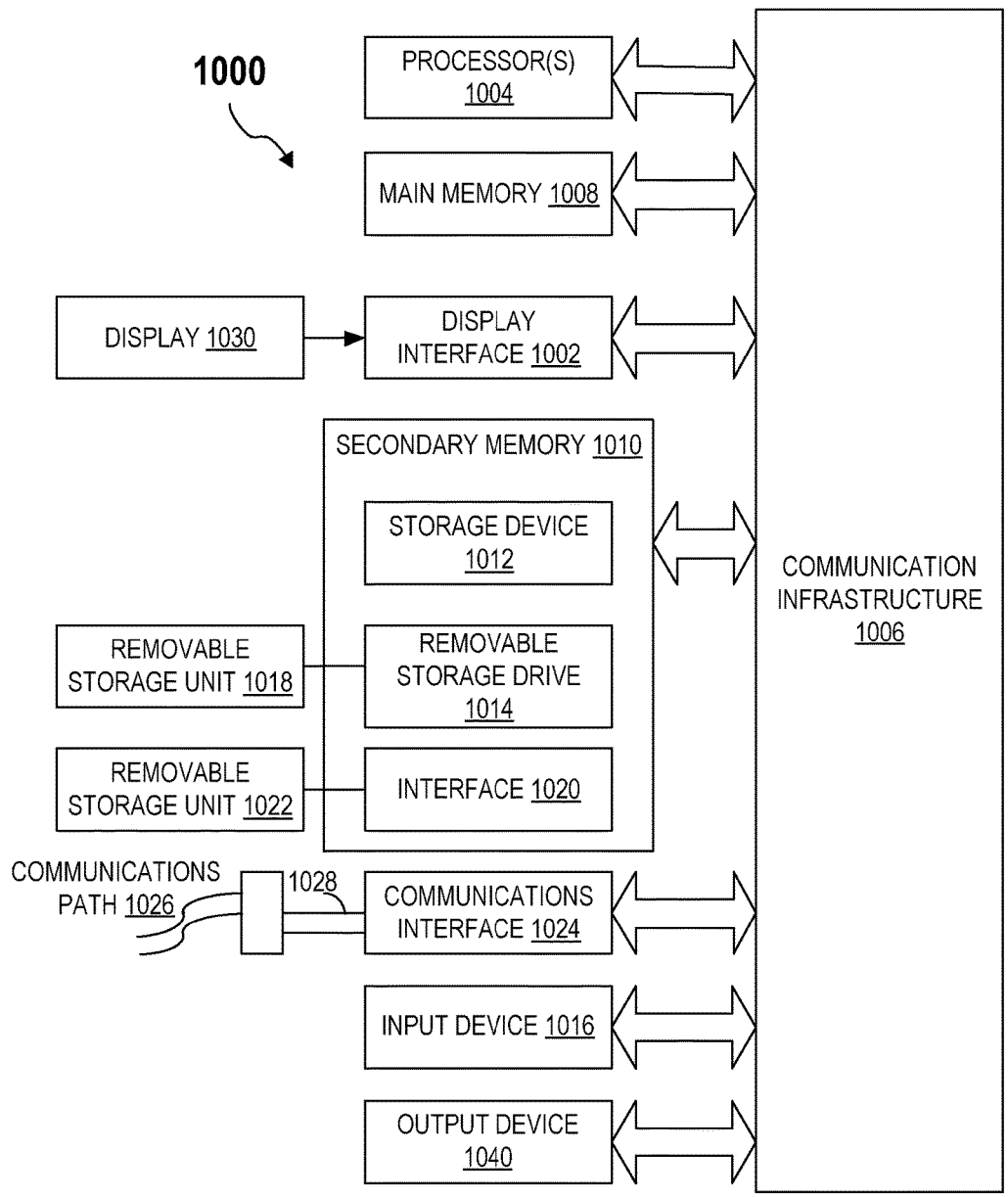
FIG. 9 depicts an illustrative embodiment of a computer system that may be used in association with, in connection with, and/or in place of, e.g., but not limited to, any of the foregoing components and/or systems according to an embodiment of the invention.

FIG. 9 depicts an illustrative embodiment of a computer system 1000 that may be used in association with, in connection with, and/or in place of, e.g., but not limited to, any of the foregoing components and/or systems. The system 10 and method of detecting, localizing, and characterizing a source of mechanical waves at one or more spatial points of interest on a structure may be implemented with one or more such computer systems 1000.

The present embodiments (or any part(s) or function(s) thereof) may be implemented using hardware, software, firmware, or a combination thereof and may be implemented in one or more computer systems or other processing systems. In an embodiment, the invention may be directed toward one or more computer systems capable of carrying out the functionality described herein. An example of a computer system 1000 is shown in FIG. 9, which depicts a block diagram of an exemplary computer system which may be useful for implementing the present invention. Specifically, FIG. 9 illustrates an example computer 1000, which in an exemplary embodiment may be, e.g., (but not limited to) a personal computer (PC) system running an operating system such as, e.g., (but not limited to) WINDOWS MOBILE™ for POCKET PC, or MICROSOFT® WINDOWS® NT/98/2000/XP/CE/7/VISTA, etc. available from MICROSOFT® Corporation of Redmond, Wash., U.S.A., SOLARIS® from SUN® Microsystems of Santa Clara, Calif., U.S.A., OS/2 from IBM® Corporation of Armonk, N.Y., U.S.A., Mac/OS from APPLE® Corporation of Cupertino, Calif., U.S.A., etc., or any of various versions of UNIX® (a trademark of the Open Group of San Francisco, Calif., USA) including, e.g., LINUX®, HPUX®, IBM AIX®, and SCO/UNIX®, etc. However, the invention may not be limited to these platforms. Instead, the invention may be implemented on any appropriate computer system running any appropriate operating system. In one exemplary embodiment, the present invention may be implemented on a computer system operating as discussed herein. Other components of the invention, such as, e.g., (but not limited to) a computing device, a communications device, a telephone, a personal digital assistant (PDA), a personal computer (PC), a handheld PC, client workstations, thin clients, thick clients, proxy servers, network communication servers, remote access devices, client computers, server computers, routers, web servers, data, media, audio, video, telephony or streaming technology servers, etc., may also be implemented using a computer such as that shown in FIG. 9.

The computer system 1000 may include one or more processors, such as, e.g., but not limited to, processor(s) 1004. The processor(s) 1004 may be connected to a communication infrastructure 1006 (e.g., but not limited to, a communications bus, cross-over bar, or network, etc.). Various exemplary software embodiments may be described in terms of this exemplary computer system. After reading this description, it will become apparent to a person skilled in the relevant art(s) how to implement the invention using other computer systems and/or architectures.

Computer system 1000 may include a display interface 1002 that may forward, e.g., but not limited to, graphics, text, and other data, etc., from the communication infrastructure 1006 (or from a frame buffer, etc., not shown) for display on the display unit 1030.

The computer system 1000 may also include, e.g., but may not be limited to, a main memory 1008, random access memory (RAM), and a secondary memory 1010, etc. The secondary memory 1010 may include, for example, (but may not be limited to) one or more hard disk or solid state drives 1012 and/or a removable storage drive 1014, representing a floppy diskette drive, a magnetic tape drive, an optical disk drive, a magneto-optical disk drive, a compact disk drive CD-ROM, a digital versatile disk (DVD), a write once read many (WORM) device, a flash memory device, etc. The removable storage drive 1014 may, e.g., but not limited to, read from and/or write to a remote or removable storage unit 1018 in a well-known manner. Removable storage unit 1018, also called a program storage device or a computer program product, may represent, e.g., but not limited to, a floppy disk, a magnetic tape, an optical disk, a magneto-optical disk, a compact disk, a flash memory device, etc. which may be read from and written to by removable storage drive 1014. As will be appreciated, the removable storage unit 1018 may include a computer usable storage medium having stored therein computer software and/or data.

In alternative exemplary embodiments, secondary memory 1010 may include other similar devices for allowing computer programs or other instructions to be loaded into computer system 1000. Such devices may include, for example, a removable storage unit 1022 and an interface 1020. Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, and other removable storage units 1022 and interfaces 1020, which may allow software and data to be transferred from the removable storage unit 1022 to computer system 1000.

Computer 1000 may also include an input device 1016 such as, e.g., (but not limited to) a mouse or other pointing device such as a digitizer, a keyboard or other data entry device (none of which are labeled), and/or a touchscreen integrated with display 1030, etc.

Computer 1000 may also include output devices 1040, such as, e.g., (but not limited to) display 1030, and display interface 1002. Computer 1000 may include input/output (I/O) devices such as, e.g., (but not limited to) communications interface 1024, cable 1028 and communications path 1026, etc. These devices may include, e.g., but not limited to, a network interface card, and modems (neither are labeled). Communications interface 1024 may allow software and data to be transferred between computer system 1000 and external devices. Examples of communications interface 1024 may include, e.g., but may not be limited to, a modem, a network interface (such as, e.g., an Ethernet card), a communications port, a Personal Computer Memory Card International Association (PCMCIA) slot and card, a transceiver, a global positioning system receiver, etc. Software and data transferred via communications interface 1024 may be in the form of signals 1028 which may be electronic, electromagnetic, optical or other signals capable of being received by communications interface 1024. These signals 1028 may be provided to communications interface 1024 via, e.g., but not limited to, a communications path 1026 (e.g., but not limited to, a channel). This channel 1026 may carry signals 1028, which may include, e.g., but not limited to, propagated signals, and may be implemented using, e.g., but not limited to, wire or cable, fiber optics, a telephone line, a cellular link, an radio frequency (RF) link and other communications channels, etc.

In this document, the terms "computer program medium" and "computer readable medium" may be used to generally refer to non-transitory media such as, e.g., but not limited to removable storage drive 1014, a hard disk installed in hard disk drive, a solid state drive, and/or other storage device 1012, etc. These computer program products may provide software to computer system 1000. The invention may be directed to such computer program products.

An algorithm is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, variables, symbols, characters, terms, numbers or the like. It should be understood, however, that all of these and similar terms are to be associated with the appropriate physical quantities and are merely convenient labels applied to these quantities.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors.

Embodiments of the present invention may include apparatuses and/or devices for performing the operations herein. An apparatus may be specially constructed for the desired purposes, or it may comprise a general purpose device selectively activated or reconfigured by a program stored in the device.

Embodiments of the invention may be implemented in one or a combination of hardware, firmware, and software. Embodiments of the invention may also be implemented as instructions stored on a machine-readable medium, which may be read and executed by a computing platform to perform the operations described herein. A machine-readable medium may include any tangible, non-transitory mechanism for storing or transmitting information in a form readable by a machine (e.g., a computer). For example, an exemplary machine-readable storage medium may include, e.g., but not limited to, read only memory (ROM); random access memory (RAM); magnetic disk storage media; optical storage media; magneto-optical storage media; and flash memory devices.

Computer programs (also called computer control logic) may include object oriented computer programs, and may be stored in main memory 1008 and/or the secondary memory 1010 and/or removable storage drive 1014, removable storage unit 1018, removable storage unit 1022, also called computer program products. Such computer programs, when executed, may enable the computer system 1000 to perform the features of the inventive embodiments discussed herein. In particular, the computer programs, when executed, may enable the processor or processors 1004 to perform steps for passively detecting, localizing, and/or characterizing a mechanical wave source at one or more spatial points of interest on a structure and/or for computing an estimated spatial channel impulse response at the one or more spatial points of interest based on collected data. For example, the processor or processors 1004 may output signals to excite one or more of the plurality of transducers 14 on the structure 12. Alternatively, or in addition, the processor or processors 1004 may receive and process signals from one or more of the plurality of transducers 14 on the structure 12 and/or from the movable transducer 20 according to the embodiments described herein.

In another exemplary embodiment, the invention may be directed to a computer program product comprising a computer readable medium having control logic (computer software) stored therein. The control logic, when executed by the processor 1004, may cause the processor 1004 to perform the functions of the invention as described herein. In another exemplary embodiment where the invention may be implemented using software, the software may be stored in a computer program product and loaded into computer system 1000 using, e.g., but not limited to, removable storage drive 1014, hard drive 1012 or communications interface 1024, etc. The control logic (software), when executed by the processor 1004, may cause the processor 1004 to perform the functions of the invention as described herein. The computer software may run as a standalone software application program running atop an operating system, may be integrated into the operating system, or may be integrated into another software program.

In yet another embodiment, the invention may be implemented primarily in hardware using, for example, but not limited to, hardware components such as one or more application specific integrated circuits (ASICs), field programmable gate-arrays (FPGAs), or other devices, etc. Implementation of a hardware device capable of performing the functions described herein will be apparent to persons skilled in the relevant art(s).

In another exemplary embodiment, the invention may be implemented primarily in firmware.

In yet another exemplary embodiment, the invention may be implemented using a combination of any of, e.g., but not limited to, hardware, firmware, and software, etc.

The exemplary embodiment of the present invention makes reference to, e.g., but not limited to, communications links, wired, and/or wireless networks. Wired networks may include any of a wide variety of well-known wired connections for coupling sensors, processors, and other devices together. Exemplary wireless network types may include, e.g., but not limited to, code division multiple access (CDMA), spread spectrum wireless, orthogonal frequency division multiplexing (OFDM), 1G, 2G, 3G, 4G wireless, Bluetooth, Infrared Data Association (IrDA—a standard method for devices to communicate using infrared light pulses), shared wireless access protocol (SWAP), "wireless fidelity" (Wi-Fi), WIMAX, and other IEEE standard 802.11-compliant wireless local area network (LAN), 802.16-compliant wide area network (WAN), and ultrawideband (UWB) networks, etc.

According to an embodiment, the methods set forth herein may be performed by one or more computer processor(s) adapted to process program logic, which may be embodied on a computer accessible storage medium, which when such program logic is executed on the exemplary one or more processor(s) may perform such steps as set forth in the methods.

While various embodiments of the present invention have been described above, it should be understood that they have been presented by way of example only, and not limitation. Although the foregoing description is directed to example embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A method of estimating and storing for subsequent, non-contemporaneous use, one or more spatial channel impulse responses corresponding to one or more spatial points of interest on a structure when the structure is in a known state comprising:
    collecting first data at one or more spatial points of interest on the structure using a movable transducer, used only in this step, wherein collecting first data includes individually exciting at least one fixed transducer on the structure with a known excitation function and recording measurements at the one or more spatial points of interest with the movable transducer;
    computing one or more spatial channel impulse response estimates for each of the one or more spatial points of interest based on the collected first data; and
    storing said spatial channel impulse response estimates for subsequent, non-contemporaneous use after the structure has transitioned to an unknown state.

2. The method according to claim 1, wherein the computing one or more spatial channel impulse response estimates includes decomposing the collected first data into one or more data sets having mode and/or directional specificity.

3. The method according to claim 1, wherein the movable transducer is configured to record measurements with mode and/or directional specificity.

4. The method according to claim 1, wherein the computing one or more spatial channel impulse response estimates includes deconvolution of the known excitation signal and/or transfer function of the movable sensor.

5. The method according to claim 1, wherein the computing one or more spatial channel impulse response estimates includes utilizing the collected first data in unprocessed form.

6. A system for detecting, localizing, and/or characterizing a source of mechanical waves at one or more spatial points of interest on a structure, comprising:
    at least one transducer affixed to the structure, wherein the at least one fixed transducer on the structure is configured to
        individually transmit a known excitation function into the structure when the structure is in a known state; and
        record a signal received from one or more mechanical wave source events originating within the structure when the structure is in an unknown state
    a movable transducer configured to record first data when the structure is in a known state at one or more spatial points of interest during individual excitement of the at least one fixed transducer on the structure;
    a storage device capable of storing one or more spatial channel impulse response estimates, wherein each spatial channel impulse response estimate corresponds to one of the one or more spatial points of interest on the structure;
    a processor coupled to the at least one fixed transducer on the structure, wherein the processor is configured to
        collect first data at the one or more spatial points of interest on the structure by receiving and processing measurements taken using the movable transducer at the one or more spatial points of interest during individual excitement of the at least one fixed transducer on the structure while the structure is in a known state
        compute one or more spatial channel impulse response estimates, each corresponding to one of the one or more spatial points of interest based on the collected first data
        store said spatial channel impulse response estimates for subsequent, non-contemporaneous use when the structure has transitioned to an unknown state
        collect second data from the at least one fixed transducer on the structure when the structure is in an unknown state, the collected second data including the recorded signal received from the one or more mechanical wave source events originating within the structure; and
        combine the collected second data with one or more previously estimated and stored spatial channel impulse response estimates to detect, localize, and/or characterize one or more mechanical wave sources at the one or more spatial points of interest on the structure.

7. The system of claim 6, wherein the movable transducer is further configured to record mode-specific and/or directional measurements taken at the one or more spatial points of interest.

8. The system of claim 6, wherein the processor is further configured to decompose the data recorded from the movable transducer, at the one or more spatial points of interest into mode-specific and/or directional components.

9. The system of claim 6, wherein the at least one fixed transducer on the structure comprises a plurality of transducers spaced from one another on the structure, and wherein one or more of the plurality of fixed transducers on the structure are configured to record signals received from the one or more mechanical wave source events.

10. The system of claim 9, wherein the processor is further configured to combine the collected second data recorded from the plurality of transducers and/or from multiple mechanical wave source events on the structure.

11. The system of claim 6, wherein the processor is further configured to use deconvolution, cross-correlation, weighted cross-correlation, regularized deconvolution, Weiner deconvolution, or a mathematically equivalent operation to combine the collected second data with one or more spatial channel impulse response estimates.

12. A method of detecting, localizing, and/or characterizing one or more mechanical wave sources originating from one or more spatial points of interest on a structure, comprising:
    collecting first data while the structure is in a known state at one or more spatial points of interest on the structure using a movable transducer, used only in this step, wherein collecting first data includes individually exciting at least one fixed transducer on the structure with a known excitation function and recording measurements at the one or more spatial points of interest with the movable transducer;
    computing one or more spatial channel impulse response estimates for each of the one or more spatial points of interest based on the collected first data;
    storing said spatial channel impulse response estimates;
    subsequently collecting second data after the structure has transitioned to an unknown state from at least one fixed transducer on the structure in response to one or more mechanical wave source events originating within the structure; and
    combining the collected second data with one or more spatial channel impulse response estimates to detect, localize, and/or characterize one or more mechanical wave sources at the one or more spatial points of interest on the structure.

13. The method according to claim 12, wherein computing one or more spatial channel impulse response estimates includes decomposing the collected first data into one or more data sets with mode and/or directional specificity.

14. The method according to claim 12, wherein the movable transducer is configured to record measurements with mode and/or directional specificity.

15. The method according to claim 12, wherein the at least one fixed transducer on the structure comprises a plurality of transducers spaced from one another on the structure.

16. The method according to claim 12, wherein the combining the collected second data with one or more spatial channel impulse response estimates comprises
    utilizing deconvolution, cross-correlation, weighted cross-correlation, regularized deconvolution, Weiner deconvolution, or other mathematically equivalent operations to generate one or more combined signals for one or more of the at least one transducer.

17. The method according to claim 16, wherein the combining the collected second data with one or more spatial channel impulse response estimates further comprises
    combining the combined signals for two or more of the at least one fixed transducer on the structure through a weighted summation operation.

18. The method according to claim 17, wherein the weighted summation operation includes weighting coefficients determined through an adaptive algorithm.

* * * * *